(12) United States Patent
Yoshida et al.

(10) Patent No.: US 9,433,567 B2
(45) Date of Patent: Sep. 6, 2016

(54) SKIN COSMETIC COMPOSITION

(71) Applicant: Kao Corporation, Chuo-ku (JP)

(72) Inventors: Tomokazu Yoshida, Suginami-ku (JP); Hidehiro Nagasawa, Ichikawa (JP)

(73) Assignee: KAO CORPORATION, Chuo-ku (JP)

( * ) Notice: Subject to any disclaimer, the term of this patent is extended or adjusted under 35 U.S.C. 154(b) by 285 days.

(21) Appl. No.: 14/291,755

(22) Filed: May 30, 2014

(65) Prior Publication Data

US 2015/0110840 A1    Apr. 23, 2015

Related U.S. Application Data

(60) Provisional application No. 61/892,088, filed on Oct. 17, 2013.

(51) Int. Cl.

| | |
|---|---|
| *A61K 31/74* | (2006.01) |
| *A61K 8/02* | (2006.01) |
| *A61K 31/20* | (2006.01) |
| *A61K 8/36* | (2006.01) |
| *A61K 8/19* | (2006.01) |
| *A61K 8/34* | (2006.01) |
| *A61K 8/37* | (2006.01) |
| *A61K 8/41* | (2006.01) |
| *A61K 8/44* | (2006.01) |
| *A61K 8/891* | (2006.01) |
| *A61K 8/92* | (2006.01) |
| *A61Q 19/00* | (2006.01) |
| *A61Q 19/08* | (2006.01) |

(52) U.S. Cl.
CPC ............ *A61K 8/361* (2013.01); *A61K 8/0204* (2013.01); *A61K 8/19* (2013.01); *A61K 8/34* (2013.01); *A61K 8/342* (2013.01); *A61K 8/36* (2013.01); *A61K 8/37* (2013.01); *A61K 8/41* (2013.01); *A61K 8/44* (2013.01); *A61K 8/891* (2013.01); *A61K 8/92* (2013.01); *A61Q 19/00* (2013.01); *A61Q 19/08* (2013.01); *A61K 2800/59* (2013.01)

(58) Field of Classification Search
None
See application file for complete search history.

(56) References Cited

U.S. PATENT DOCUMENTS

| | | |
|---|---|---|
| 2012/0108661 A1 | 5/2012 | Orita et al. |
| 2013/0236411 A1 | 9/2013 | Ishikubo et al. |
| 2014/0100276 A1 | 4/2014 | Orita et al. |

FOREIGN PATENT DOCUMENTS

| | | |
|---|---|---|
| CN | 102724953 A | 10/2012 |
| CN | 103179949 A | 6/2013 |
| EP | 1 681 062 A1 | 7/2006 |
| EP | 2 452 668 A1 | 5/2012 |
| EP | 2 630 949 A1 | 8/2013 |
| JP | 6-345633 | 12/1994 |
| JP | 7-223934 | 8/1995 |
| JP | 2003-12486 | 1/2003 |
| JP | 2006-290751 A | 10/2006 |
| JP | 2006-312622 A | 11/2006 |
| JP | 2007-9199 | 1/2007 |

OTHER PUBLICATIONS

Genji Imokawa et al. "Stratum Corneum Lipids Serve as a Bound-Water Modulator", The Journal of Investigative Dermatology, vol. 96, 1991, 7 pages.
Teruhisa Kaneko et al. "Preparation and Characteristics of Arginine Oleate Liquid Crystal Holding a Large Amount of Water", Journal of Oleo Science, vol. 54, No. 6, 2005, 9 pages.
International Search Report and Written Opinion issued Mar. 11, 2015 in PCT/JP2014/077765 (submitting English translation only).

*Primary Examiner* — Jeffrey T Palenik
(74) *Attorney, Agent, or Firm* — Oblon, McClelland, Maier & Neustadt, L.L.P.

(57) ABSTRACT

A skin cosmetic composition comprising the following components (A), (B), (C), (D), (E) and (F):
 (A) from 0.5 to 6% by mass of a linear saturated fatty acid having 12 to 22 carbon atoms,
 (B) from 0.01 to 5% by mass of an organic base,
 (C) from 0.01 to 1% by mass of an inorganic base,
 (D) from 0.5 to 6% by mass of a linear saturated alcohol having 12 to 22 carbon atoms,
 (E) from 0.1 to 20% by mass of an oil agent, and
 (F) water,
in which the total amount of components (A) and (D), [(A)+(D)], is from 2.5 to 12% by mass; the mass ratio (A)/[(A)+(D)], which is the mass ratio of component (A) to the total amount of components (A) and (D), [(A)+(D)], is from 0.2 to 0.7; the molar ratio (B)/[(B)+(C)], which is the molar ratio of component (B) to the total amount of components (B) and (C), [(B)+(C)], is from 5 to 60 mol %; and the molar ratio [(B)+(C)]/(A), which is the molar ratio of the total amount of components (B) and (C), [(B)+(C)], to component (A), is from 10 to 80 mol %.

15 Claims, 2 Drawing Sheets

EXAMPLE 7: MIXTURE OF CONCENTRIC LAMELLA AND BULK LAMELLA

Observation of bulk lamella (using polarizing plate) — Bulk lamella

Observation of concentric lamella (without using polarizing plate) — Concentric lamella, Oil agent

COMPARATIVE EXAMPLE 10: ONLY CONCENTRIC LAMELLA

SKIN COSMETIC COMPOSITION

FIELD OF THE INVENTION

The present invention relates to a skin cosmetic composition.

BACKGROUND OF THE INVENTION

For keeping youngful appearance by protecting the skin from the exterior environment such as dryness and physical stimuli and keeping the skin soft by moisturizing it, cosmetic compositions comprising a polyol such as glycerin and oil agents and moisturizing agents such as amino acids and hyaluronic acid have been developed. These cosmetic compositions protect the skin, owing to application of an emulsion layer containing oil and water to the skin, from outside stimuli and prevent evaporation of moisture from the interior of the skin, and simultaneously, supply a certain amount of water to the skin, contributing to improvement of rough skin and dry skin.

In the meantime, cosmetic compositions comprising a keratinocyte intercellular lipid component such as ceramide and further having a lamellar structure similar to that of an intercellular lipid are proposed (Non-Patent Document 1, Patent Document 1).

However, if an amphipathic solid lipid having a high melting point such as a ceramide is added to an oil-in-water emulsion, separation of the emulsion and gelatinization are likely to occur with the passage of time. Since it is difficult to keep a composition stable as mentioned above, there are many limitations in a production method and formulation.

Since a ceramide tends to be crystallized, it has been proposed to add a large amount of emulsifier with respect to an amount of a ceramide (Patent Document 2, Patent Document 3); however, these methods have a problem in poor adaptability to the skin during use.

In addition, since a ceramide itself is expensive, there is a problem in terms of the versatility of ceramide.

In the meantime, there is a technique known in the art for forming the lamellar structure without using a ceramide, and the like. This is a technique using an arginine salt of a fatty acid (Non-Patent Document 2).

Furthermore, cosmetic compositions using an arginine salt of a fatty acid in combination with a higher alcohol and a surfactant have been studied (for example, Patent Document 4).

Non-Patent Document 1: The journal of investigative dermatology, vol. 96(6), 845-851 (1991)
Non-Patent Document 2: J. Oleo. Sci., vol. 54(6), 325-333 (2005)
Patent Document 1: JP-A-H6-345633
Patent Document 2: JP-A-2003-12486
Patent Document 3: JP-A-H7-223934
Patent Document 4: JP-A-2007-9199

SUMMARY OF THE INVENTION

The present invention relates to a skin cosmetic composition comprising the following components (A), (B), (C), (D), (E) and (F):
(A) from 0.5 to 6% by mass of a linear saturated fatty acid having 12 to 22 carbon atoms,
(B) from 0.01 to 5% by mass of an organic base,
(C) from 0.01 to 1% by mass of an inorganic base,
(D) from 0.5 to 6% by mass of a linear saturated alcohol having 12 to 22 carbon atoms,
(E) from 0.1 to 20% by mass of an oil agent, and
(F) water,
in which the total amount of components (A) and (D), [(A)+(D)], is from 2.5 to 12% by mass; the mass ratio (A)/[(A)+(D)], which is the mass ratio of component (A) to the total amount of components (A) and (D), [(A)+(D)], is from 0.2 to 0.7; the molar ratio (B)/[(B)+(C)], which is the molar ratio of component (B) to the total amount of components (B) and (C), [(B)+(C)], is from 5 to 60 mol %; and the molar ratio [(B)+(C)]/(A), which is the molar ratio of the total amount of components (B) and (C), [(B)+(C)], to component (A), is from 10 to 80 mol %.

DETAILED DESCRIPTION OF THE EMBODIMENTS

Figure 1:
FIG. 1 is a photograph showing a structure of the skin cosmetic composition of Example 7 observed by a polarizing microscope.
Figure 1:
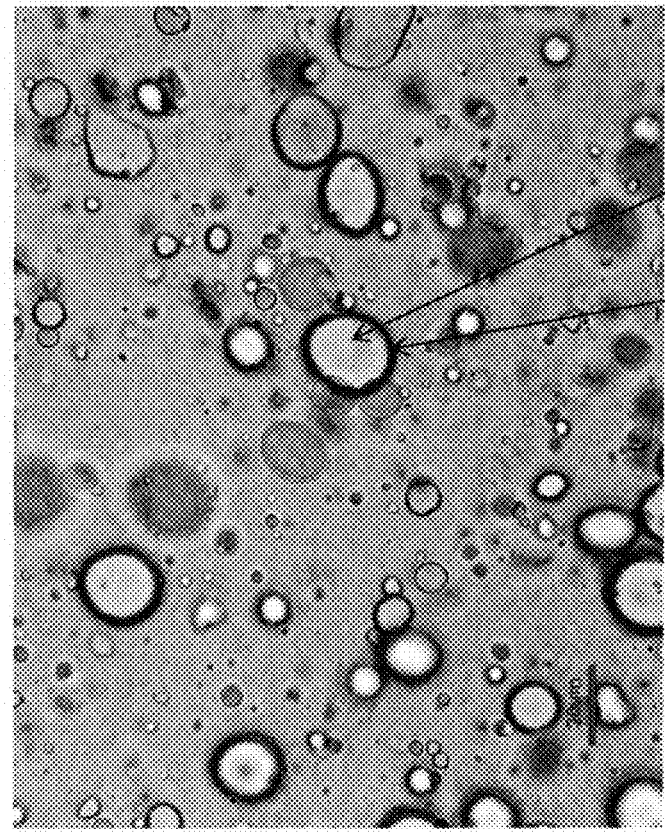

The present invention relates to a skin cosmetic composition, which forms a cosmetic coating film having a lamellar structure on the skin surface after the cosmetic composition is applied to the skin, and which has thereby high water-holding capacity (in other words, high moisture-retaining property) against moisture evaporation from the skin under a low-humidity environment and high retention of gloss skin, and which simultaneously provides no slimy feeling when applied, suppresses foaming and whitening when applied, and provides excellent storage stability without precipitation of crystals.

The present inventors found that a skin cosmetic composition having excellent water-holding capacity and durability of glossy skin, providing no slimy feeling when applied, suppressing foaming and having excellent storage stability, can be obtained by combining a predetermined saturated fatty acid, a saturated alcohol, an organic base, an inorganic base, an oil agent and water, in a predetermined ratio.

The skin cosmetic composition of the present invention has a lamellar structure, and one feature of the present invention is to have two types of lamellar structures. One of them is a lamella (hereinafter referred to as a concentric lamella), which is formed around the oil agent so as to surround the oil agent; whereas, the other one is a lamella (hereinafter referred to as a bulk lamella), which is formed as a continuous phase in the cosmetic composition. These lamellas have a key feature in that they are co-present like sea-islands such that concentric lamellas are present in the bulk lamella. The co-presence of the bulk lamella and concentric lamellas lasts long even in the coating film of the composition formed on the skin after application of the composition to the skin. In contrast, it is conventionally known that many cosmetic compositions comprise either one of the lamellar structures or that lamellas are no longer present in the coating film formed after application. Accordingly, it is presumed that such structures and characteristics of lamellas contribute to excellent effects of the present invention, including water-holding capacity and durability of glossy skin, no slimy feeling when applied, suppression of foaming and uniform application and good adaptability to the skin. High water-holding capacity means that the moisture-retaining property is excellent. The bulk lamella and concentric lamellas can be observed by a polarizing microscope (sample thickness: 25 mm). That is, if a structure looks wholly bright, it indicates the presence of a bulk lamella; whereas if Maltese Crosses are observed, it indicates the presence of concentric lamellas.

The skin cosmetic composition of the present invention, since it is excellent in storage stability, has a stable lamellar structure without precipitation of crystals and further forms a dry film having a lamellar structure on the skin surface when applied. The dry film is excellent in moisture-retaining property and durability of glossy skin and the skin cosmetic composition is applied without slimy feeling and suppresses foaming.

(A) Linear Saturated Fatty Acid Having 12 to 22 Carbon Atoms:

Component (A) to be used in the present invention is a linear saturated fatty acid having 12 to 22 carbon atoms. Examples of the linear saturated fatty acid include lauric acid, myristic acid, palmitic acid, stearic acid and behenic acid. Among them, a linear saturated fatty acid having 14 to 22 carbon atoms is preferable, a linear saturated fatty acid having 16 to 22 carbon atoms is more preferable, and at least either one of palmitic acid and stearic acid is even more preferable in consideration that a stable lamellar structure is formed in the cosmetic composition and that a bulk lamella and a concentric lamella are formed as the lamellar structure. Furthermore, in consideration of stability of a lamellar structure and formation of a bulk lamella and concentric lamellas as the lamellar structure, stearic acid is further more preferable.

As component (A), one or two or more compounds can be used. Component (A) can be neutralized with components (B) and (C) described later to form a lamellar structure in a cosmetic composition. Component (A) is present in the form of a fatty acid or a salt thereof in a cosmetic composition, and the content of component (A) is expressed in terms of a fatty acid in the present invention.

In the skin cosmetic composition of the present invention, it is preferable that component (A) includes two or more linear saturated fatty acids having 12 to 22 carbon atoms different from each other in the number of carbon atoms by two or more in order to improve the moisture-retaining property.

Owing to two or more linear saturated fatty acids different from each other in the number of carbon atoms by two or more contained in a skin cosmetic composition, it is considered that the density of the lamellar structure improves and water-holding capacity increases, in other words, the moisture-retaining property improves.

Of the two or more linear saturated fatty acids having 12 to 22 carbon atoms different from each other in the number of carbon atoms by two or more, the linear saturated fatty acid having 12 to 22 carbon atoms in which the number of carbon atoms is larger (referred to also as a high carbon-atom saturated fatty acid in the present invention) preferably has 14 to 22 carbon atoms, more preferably 16 to 20 carbon atoms and even more preferably 18 carbon atoms in order to improve the moisture-retaining property. In contrast, the linear saturated fatty acid having 12 to 22 carbon atoms in which the number of carbon atoms is smaller (referred to also as a low carbon-atom saturated fatty acid in the present invention) preferably has 12 to 20 carbon atoms, more preferably 12 to 18 carbon atoms and even more preferably 14 to 16 carbon atoms from the same point of view.

If component (A) contains two or more linear saturated fatty acids different from each other in the number of carbon atoms by two or more, component (A) preferably contains at least a linear saturated fatty acid having 16 or 18 carbon atoms, in other words, palmitic acid or stearic acid, and more preferably contains at least a linear saturated fatty acid having 18 carbon atoms, i.e., stearic acid, from the same points of view.

The mass ratio of stearic acid contained in component (A) is preferably from 0.2 to 0.8 and more preferably from 0.4 to 0.6 in order to improve the moisture-retaining property.

The content of component (A) is 0.5% by mass or more, preferably 1.5% by mass or more and more preferably 1.8% by mass or more, and 6% by mass or less, preferably 4% by mass or less and more preferably 3.8% by mass or less based on the total composition in order to form a stable lamellar structure in the cosmetic composition and form a bulk lamella and concentric lamellas as the lamella structure. Also, the content of component (A) is from 0.5 to 6% by mass, preferably from 1.5 to 4% by mass and more preferably from 1.8 to 3.8% by mass based on the total composition.

(B) Organic Base:

Component (B) to be used in the present invention is an organic base. Examples of the organic base include an alkyl amine having an alkyl group having 1 to 6 carbon atoms, an alkanolamine having an alkyl group having 1 to 6 carbon atoms and a basic amino acid. Component (B) serves as a neutralizing agent for component (A).

Examples of the alkyl amine include methylamine, ethylamine, propylamine, butylamine, hexylamine, dimethylamine and diethylamine. Examples of the alkanolamine include monoethanolamine, diethanolamine, triethanolamine, N-methyldiethanolamine, N,N-dimethylmonoethanolamine and aminomethyl propanol. Of them, aminomethyl propanol is preferable. Examples of the basic amino acid include lysine, histidine and arginine. Of them, arginine is preferable. As arginine, L-arginine is preferable.

Of these, in order to neutralize component (A), form a stable lamellar structure in the cosmetic composition, form a bulk lamella and concentric lamellas as the lamella structure, suppress precipitation of crystals and enhance the moisture-retaining property, an alkanolamine having an alkyl group having 1 to 6 carbon atoms or a basic amino acid having 1 to 6 carbon atoms is preferable, an alkanolamine having an alkyl group having 3 to 6 carbon atoms or a basic amino acid having 3 to 6 carbon atoms is more preferable, a basic amino acid is even more preferable, an aminomethyl propanol or arginine is even more preferable and arginine is further more preferable. As arginine, L-arginine is preferable.

As component (B), one or two or more compounds at least selected from the aforementioned organic bases can be used. In order to enhance stability of the lamellar structure of a skin cosmetic composition, suppress precipitation of crystals and enhance the moisture-retaining property, the molar ratio of component (B) to component (A) is preferably 5 mole % or more, more preferably 10 mole % or more, even more preferably 15 mole % or more and further more preferably 30 mole % or more, and preferably less than 80 mol % and more preferably 60 mole % or less.

The content of component (B) is 0.01% by mass or more, preferably 0.02% by mass or more and more preferably 0.1% by mass or more, and 5% by mass or less, preferably 0.8% by mass or less and more preferably 0.4% by mass or less based on the total composition in order to enhance stability of a lamella structure in the skin cosmetic composition and enhance a moisture-retaining property. Also, the content of component (B) is from 0.01 to 5% by mass, preferably from 0.02 to 0.8% by mass and more preferably from 0.1 to 0.4% by mass based on the total composition.

Note that component (B) can react with component (A) and another acid to form a salt in the cosmetic composition, and the content of component (B) is expressed in terms of an organic base in the present invention.

(C) Inorganic Base:

Component (C) to be used in the present invention is an inorganic base. Examples of the inorganic base include an alkali metal hydroxide such as sodium hydroxide or potassium hydroxide. Component (C) serves as a neutralizing agent for component (A).

Of them, sodium hydroxide or potassium hydroxide is preferable and sodium hydroxide is more preferable in order to neutralize component (A), form a stable lamellar structure in a cosmetic composition and form a bulk lamella and concentric lamellas as the lamella structure.

As component (C), one or two or more compounds at least selected from the aforementioned inorganic bases can be used. In order to enhance stability of lamellar structure of a skin cosmetic composition and enhance a moisture-retaining property, the molar ratio of component (C) to component (A) is preferably 5 mole % or more, more preferably 10 mole % or more, even more preferably 15 mole % or more and further more preferably 30 mole % or more, and preferably less than 80 mol % and more preferably 60 mole % or less.

The content of component (C) is 0.01% by mass or more, preferably 0.04% by mass or more and more preferably 0.08% by mass or more, and 1% by mass or less, preferably 0.3% by mass or less and more preferably 0.2% by mass or less based on the total composition in order to enhance stability of a lamellar structure of the skin cosmetic composition and enhance a moisture-retaining property. The content of component (C) is from 0.01 to 1% by mass, preferably from 0.04 to 0.3% by mass and more preferably from 0.08 to 0.2% by mass based on the total composition.

Note that component (C) can react with component (A) and another acid to form a salt, and the content of component (C) is expressed in terms of an inorganic base in the present invention.

In the present invention, the molar ratio of {(B)/[(B)+(C)]}, which is the molar ratio of component (B) to the total amount of components (B) and (C), [(B)+(C)], is from 5 to 60 mol %, preferably from 8 to 50 mol %, more preferably from 10 to 45 mol % and even more preferably from 15 to 40 mol % in order to suppress crystallization, form a film having excellent water-holding capacity and suppress slimy feeling.

The molar ratio [(B)+(C)]/(A), which is the molar ratio of the total amount of components (B) and (C) to component (A), which represents degree of neutralization, is from 10 to 80 mol %, preferably from 20 to 70 mol %, more preferably from 25 to 65 mol % and even more preferably from 30 to 60 mol % in order to form two types of lamellar structures (i.e., a bulk lamella and concentric lamellas), form a film having excellent water-holding capacity and suppress crystallization and foaming.

From the same points of view as above, as the combination of component (B) and component (C), a combination of aminomethyl propanol or arginine as component (B) and sodium hydroxide or potassium hydroxide as component (C) is preferable and a combination of arginine as component (B) and sodium hydroxide as component (C) is more preferable.

(D) Linear Saturated Alcohol Having 12 to 22 Carbon Atoms:

Component (D) to be used in the present invention is a linear saturated alcohol having 12 to 22 carbon atoms. Examples of the linear saturated alcohol include lauryl alcohol, myristyl alcohol, cetyl alcohol, stearyl alcohol and behenyl alcohol. Of them, a linear saturated alcohol having 14 to 22 carbon atoms is preferable and a linear saturated alcohol having 16 to 22 carbon atoms is more preferable. In order to stabilize a lamellar structure formed from component (A) in the cosmetic composition and form a bulk lamella and concentric lamellas as the lamellar structure, cetyl alcohol or stearyl alcohol is further preferable and cetyl alcohol and stearyl alcohol are further more preferably contained in the cosmetic composition. In the case of containing cetyl alcohol and stearyl alcohol in the cosmetic composition, they are each added independently or in the form of a mixture. Alternatively, cetostearyl alcohol, which is a mixture of them, may be added.

As component (D), one or two or more compounds at least selected from the linear saturated alcohols having 12 to 22 carbon atoms mentioned above can be used. In order to stabilize a lamellar structure in a cosmetic composition and form a bulk lamella and concentric lamellas as the lamellar structure, the content of component (D) is 0.5% by mass or more, preferably 1% by mass or more and more preferably 1.5% by mass or more, and 6% by mass or less, preferably 5.5% by mass or less and more preferably 5.2% by mass or less based on the total composition. Also, the content of component (D) is from 0.5 to 6% by mass, preferably from 1 to 5.5% by mass and more preferably from 1.5 to 5.2% by mass based on the total composition.

In the present invention, the total amount of components (A) and (D), [(A)+(D)], is 2.5% by mass or more, preferably 3% by mass or more and more preferably 4.5% by mass or more, and 12% by mass or less, preferably 9.5% by mass or less and more preferably 8% by mass or less in order to enhance storage stability of the cosmetic composition. Also, the total amount of components (A) and (D), [(A)+(D)], is from 2.5 to 12% by mass, preferably from 3 to 9.5% by mass and more preferably from 4.5 to 8% by mass.

Furthermore, the mass ratio {(A)/[(A)+(D)]}, which is the mass ratio of component (A) to the total amount of components (A) and (D), [(A)+(D)], is 0.2 or more, preferably 0.25 or more and more preferably 0.3 or more, and 0.7 or less, preferably 0.6 or less and more preferably 0.5 or less in order to form a lamella in a cosmetic composition as well as suppress crystallization and enhance a moisture-retaining property. Also, (A)/[(A)+(D)], which is the mass ratio of component (A) to the total amount of components (A) and (D), [(A)+(D)], is from 0.2 to 0.7, preferably from 0.25 to 0.6 and more preferably from 0.3 to 0.5.

(E) Oil Agent:

Component (E) to be used in the present invention is an oil agent except components (A) and (D) such as hydrocarbon oils such as liquid paraffin, squalene and vaseline; ether oils such as cetyl dimethylbutyl ether, ethylene glycol dioctyl ether and glycerol monooleyl ether; ester oils such as octyldodecyl myristate, isopropyl palmitate, butyl stearate, di-2-ethylhexyl adipate, neopentyl glycol dicaprate, trioctanoin and alkyl benzoate; silicone oils such as a dimethylpolysiloxane, a cyclic dimethylpolysiloxane, a methylphenylpolysiloxane, an amino-modified silicone, a carboxy-modified silicone, an alcohol-modified silicone, an alkyl-modified silicone, a polyether-modified silicone and a fluorine-modified silicone; and fluorine oils such as perfluoroalkylethyl phosphate, perfluoroalkyl polyoxyethylene phosphate, perfluoropolyether and polytetrafluoroethylene. These oil agents may be derived from plants.

Of them, in order to retain glossy skin, a hydrocarbon oil, an ester oil and a silicone oil are preferable. As the hydrocarbon oil, at least one selected from the group consisting of liquid paraffin, squalene and vaseline, is preferable. As the ester oil, at least one selected from the group consisting of octyldodecyl myristate, isopropyl palmitate, butyl stearate, di-2-ethylhexyl adipate, neopentyl glycol dicaprate, trioctanoin and alkyl benzoate, is preferable. As the silicone oil, at least one selected from the group consisting of a dimethylpolysiloxane, a cyclic dimethylpolysiloxane, a methylphenylpolysiloxane, an amino-modified silicone, a carboxy-modified silicone, an alcohol-modified silicone, an alkyl-modified silicone, a polyether-modified silicone and a fluorine-modified silicone, is preferable.

As component (E), an oil agent having a refraction index of 1.46 to 1.6 is preferably included in order to impart high gloss to the skin after application of a cosmetic composition.

In the present invention, the refraction index is measured by an Abbe refractometer (NAR-2T, manufactured by ATAGO CO., LTD, measurement wavelength: 589 nm) at 25° C.

Conventionally, an oil agent having a refraction index of 1.46 to 1.6 was used in an emulsified composition obtained by mixing the oil agent with a surfactant and/or a higher alcohol. However, gloss of the dry films obtained from these cosmetic compositions was not sufficient. This is because an oil agent having a refraction index of 1.46 to 1.6 is mixed with a surfactant (crystallized after drying) and/or a higher alcohol at random, and thus a well-ordered reflective surface was not obtained. However, according to the skin cosmetic composition of the present invention, in a film, which is obtained by applying the cosmetic composition and drying it, a water phase and a surfactant phase (including an oil phase) constitute a laminate like lamella (lamellar structure). As a result, component (E) can be orderly arranged in the plane of the surfactant phase to form a well-ordered reflective surface. Furthermore, this film has a lamellar structure, a plurality of reflective surfaces can be formed. As a result, it is considered that the films formed of the skin cosmetic composition of the present invention can more highly reflect light than those formed of conventional compositions.

Examples of the oil agent having a refraction index of 1.46 to 1.6 include a hydrocarbon oil such as a highly polymerized hydrogenated polyisobutene (number average molecular weight: 1000 to 3000, refraction index: 1.49), an ester oil such as an alkyl benzoate having 10 to 22 carbon atoms (refraction index: 1.48) and silicone oil such as a methylphenylpolysiloxane (refraction index: 1.58). Of them, an ester oil is preferable, an alkyl benzoate having an alkyl group having 10 to 22 carbon atoms (refraction index: 1.48) is more preferable and an alkyl benzoate having an alkyl group having 12 to 18 carbon atoms (refraction index: 1.48) is even more preferable. The refraction index is more preferably 1.48 or more and further preferably 1.58 or less.

As component (E), one or two or more oil agents at least selected from the oil agents mentioned above can be used.

The content of component (E) is 0.1% by mass or more, preferably 0.3% by mass or more and more preferably 0.5% by mass or more, and 20% by mass or less, preferably 18% by mass or less and more preferably 16% by mass or less based on the total composition in order to improve gloss of the dry film formed of the cosmetic composition. Also, the content of component (E) is from 0.1 to 20% by mass, preferably from 0.3 to 18% by mass and more preferably from 0.5 to 16% by mass based on the total composition.

Furthermore, it is preferable that an oil agent having a refraction index of 1.46 to 1.6 is contained in order to impart high gloss to the skin after application of a cosmetic composition. The content of the oil agent having a refraction index of 1.46 to 1.6 in component (E) is preferably from 30 to 100% by mass, more preferably from 60 to 100% by mass, even more preferably from 90 to 100% by mass and further preferably substantially 100% by mass.

In the present invention, the mass ratio $\{(E)/[(A)+(D)]\}$, which is the mass ratio of component (E) to the total amount of components (A) and (D), $[(A)+(D)]$, is preferably 0.1 or more, more preferably 0.15 or more and even more preferably 0.2 or more, and preferably 3 or less, more preferably 2 or less and even more preferably 1.5 or less in order to enhance a moisture-retaining property, suppress foaming and slimy feeling and retain glossy skin. Also, the mass ratio $\{(E)/[(A)+(D)]\}$, which is the mass ratio of component (E) to the total amount of components (A) and (D), $[(A)+(D)]$, is preferably from 0.1 to 3, more preferably 0.15 to 2 and even more preferably from 0.2 to 1.5.

(F) Water:

Component (F) to be used in the present invention is water, which serves as a solvent for the cosmetic composition of the present invention. Component (F) is added as the remaining (balance) of other components. A stable lamellar structure can be formed in a cosmetic composition due to the combination of components (A) to (F).

The content of component (F) is preferably 50% by mass or more and more preferably 60% by mass or more, and preferably 95% by mass or less and more preferably 90% by mass or less based on the total composition in order to form a stable lamellar structure in the cosmetic composition and form a bulk lamella and concentric lamellas as the lamellar structure. Also, the content of component (F) is preferably from 50 to 95% by mass and more preferably from 60 to 90% by mass based on the total composition.

In the skin cosmetic composition of the present invention, a lamellar structure is formed by containing components (A) to (F). The cosmetic composition is applied to the skin, and then water is evaporated to form a cosmetic coating film on the surface of the skin. In the cosmetic coating film, a lamellar structure, in which concentric lamellas and a bulk lamella are co-present, is formed. The lamellar structure forms a film having excellent water-holding capacity and can keep a large amount of water between lamellas. As a result, the skin cosmetic composition not only suppresses moisture evaporation from the skin but also supplies water to the skin, attaining a high moisture-retaining property. Furthermore, the skin cosmetic composition of the present invention has a feature in that glossy skin can be retained for a long time. The specific reason for this is unknown; however, it is considered that an oil agent can be maintained in the skin surface by concentric lamellas co-present in the bulk lamella. Furthermore, since foaming is suppressed when the cosmetic composition is applied, a lamellar structure can be densely formed on the skin, with the result that a coating film having excellent water-holding capacity is formed. Moreover, the coating film is highly flexible and has excellent adhesion to the skin.

(G) Nonionic Surfactant:

In the present invention, a lamellar structure as mentioned above is easily formed. A nonionic surfactant can be added in order to improve stability of the lamellar structure, improve gloss and suppress foaming.

Due to addition of the nonionic surfactant, when the skin cosmetic composition of the present invention is applied to the skin by fingers, it can suppress whitening of the skin derived from fine foams produced by the friction between the skin and the fingers. As a result, the cosmetic composition applied to the skin can be sufficiently adapted to the skin.

Examples of the nonionic surfactant include ethylene glycol fatty acid esters such as ethylene glycol monostearate; polyethylene glycol fatty acid esters such as polyethylene glycol (2) monostearate; polyalkylene glycol alkyl ethers such as polyethylene glycol (5) decyl pentadecyl ether; polyethylene glycol hydrogenated castor oils such as polyethylene glycol (5) hydrogenated castor oil monoisolaurate; propylene glycol fatty acid esters; mono glycerin monofatty acid esters such as glycerin monoisostearate and glycerin monostearate; monoglycerin difatty acid esters such as glycerin distearate and glycerin dilaurate; glycerin alkyl ethers such as glycerin monoisostearyl ether and glycerin monostearyl ether; sorbitan fatty acid esters such as sorbitan monostearate; fatty acid alkanolamide; and fatty acid dialkanolamides such as lauric acid diethanolamide.

Of these nonionic surfactants, a polyalkylene glycol alkyl ether having an alkyl group having 12 to 22 carbon atoms is preferable, a polyalkylene glycol ether having an alkyl group having 12 to 18 carbon atoms is more preferable in order to suppress generation of fine foams when a cosmetic composition is applied.

Furthermore, in order to improve density of the lamellar structure and improve water-holding capacity, in other words, moisture-retaining property, the nonionic surfactant preferably has an HLB of 1 to 4. More specifically, a monoglycerin monofatty acid ester such as glycerin monostearate (HLB: 3.4); and a glycerin alkyl ether such as glycerin monostearyl ether (HLB: 4.0) are preferable.

In the present invention, the HLB value is an index indicating a hydrophilicity-lipophilicity balance (Hydrophile Lipophile Balance). In the present invention, the value calculated in accordance with the following expression provided by Oda and Teramura is used.

$$HLB = \frac{\Sigma \text{Inorganic value}}{\Sigma \text{Organic value}} \times 10 \qquad \text{[Expression 1]}$$

As component (G), one or two or more nonionic surfactants can be used. In order to enhance a moisture-retaining property, suppress slimy feeling and enhance sustention of glossy skin in addition to the aforementioned viewpoints, component (G) preferably contains at least two polyalkylene glycol ethers different from each other in the number of carbon atoms by two or more; more preferably contains at least two compounds selected from the group consisting of a polyethylene glycol ether of lauryl alcohol (laureth-3), a polyethylene glycol ether of cetyl alcohol, and a polyethylene glycol ether of stearyl alcohol; and even more preferably contains these three polyethylene glycol ethers. When two or more polyalkylene glycol ethers having an alkyl group having 12 to 18 carbon atoms are used, they may be each added independently or in the form of a mixture. Alternatively, ceteareth-20, which is a mixture of a polyethylene glycol ether of cetyl alcohol and a polyethylene glycol ether of stearyl alcohol, may be added and laureth-3 and ceteareth-20 are more preferably added.

The content of a nonionic surfactant as component (G) is preferably 0.1% by mass or more, more preferably 0.3% by mass or more and even more preferably 0.5% by mass or more, and preferably 2% by mass or less, more preferably 1.5% by mass or less and even more preferably 1.3% by mass or less based on the total composition in order to improve a moisture-retaining property, suppress slimy feeling, improve stability and suppress foaming of a cosmetic composition when it is applied to the skin. Also, the content of component (G) is preferably from 0.1 to 2% by mass, more preferably from 0.3 to 1.5% by mass and even more preferably from 0.5 to 1.3% by mass based on the total composition.

The mass ratio {[(A)+(D)]/(G)}, which is the mass ratio of the total amount of components (A) and (D), [(A)+(D)], to component (G), is preferably 3 or more, more preferably 4 or more and even more preferably 5 or more, and preferably 30 or less, more preferably 20 or less and even more preferably 10 or less in order to improve a moisture-retaining property, suppress slimy feeling, improve stability and suppress foaming of a cosmetic composition. Also, the mass ratio {[(A)+(D)]/(G)}, which is the mass ratio of the total amount of components (A) and (D), [(A)+(D)], to component (G), is preferably from 3 to 30, more preferably from 4 to 20 and even more preferably from 5 to 10.

The skin cosmetic composition of the present invention can further appropriately comprise components usually used in cosmetic compositions, other than components (A) to (G), such as a thickener, a sterilizer, a moisturizer, a humectant, a coloring agent, an antiseptic agent, a touch improver, a powder, a fragrance, an anti-inflammatory agent, a whitening agent, an antiperspirant, a UV absorber and an antioxidant.

In the present invention, the skin cosmetic composition can comprise an anionic surfactant in order to form concentric lamellas having highly dense films, improve stability of a lamellar structure, improve a moisture-retaining property, reduce oily feeling, improve durability of gloss and suppress foaming.

The anionic surfactant is selected from those excluding component (A). Examples thereof include alkyl sulfuric acid esters with 12 to 22 carbon atoms or salts thereof, such as sodium lauryl sulfate and potassium lauryl sulfate; alkyl ether sulfuric acid esters with 12 to 22 carbon atoms or salts thereof, such as polyoxyethylene lauryl sulfuric acid triethanolamine; N-acylsarcosines with 12 to 22 carbon atoms or salts thereof, such as sodium lauroylsarcosinate; alkyl phosphoric acids with 12 to 22 carbon atoms or salts thereof, such as sodium monostearyl phosphate; polyoxyethylene alkyl ether phosphoric acids with 12 to 22 carbon atoms or salts thereof, such as sodium polyoxyethylene oleyl ether phosphate and sodium polyoxyethylene stearyl ether phosphate; dialkyl sulfosuccinic acids with 12 to 24 carbon atoms or salts thereof, such as sodium di-2-ethylhexylsulfosuccinate; N-alkyloylmethyl taurine with 12 to 22 carbon atoms or salts thereof, such as sodium N-stearoyl-N-methyl taurate; and N-acyl glutaminic acid with 12 to 22 carbon atoms or salts thereof, such as sodium dilauroylglutamate, monosodium N-lauroylglutamate, sodium N-stearoyl-L-glutamate, arginine N-stearoyl-L-glutamate, sodium N-stearoylglutamate and sodium N-myristoyl-L-glutamate.

As the anionic surfactant, one or more anionic surfactants at least selected from anionic surfactants mentioned above can be used and the anionic surfactants can be used alone or in combination of two or more.

The content of the anionic surfactant is preferably 0.01% by mass or more, more preferably 0.1% by mass or more and even more preferably 0.3% by mass or more, and preferably 2% by mass or less, more preferably 1.8% by mass or less and even more preferably 1.5% by mass or less based on the total composition in order to form concentric lamellas having highly dense films, improve stability of a lamellar structure, improve a moisture-retaining property, reduce oily feeling, improve durability of gloss and suppress foaming.

The skin cosmetic composition of the present invention can further comprise a solid lipid other than components (A) and (D). The content of the solid lipid is preferably 10% by mass or less, more preferably 8% by mass or less, even more preferably 5% by mass or less and further more preferably 3% by mass or less in order to stabilize the lamellar structure.

The skin cosmetic composition of the present invention can be produced, for example, as follows. First, components (B), (C) and (F) are mixed and the mixture is dissolved at 60 to 100° C. homogeneously to give a water phase. Then, components (A), (D) and (E) are mixed and the mixture is dissolved at 60 to 100° C. homogeneously to give an oil phase. The water phase and the oil phase are mixed homogeneously, and the mixture is cooled to preferably 5 to 30° C., more preferably 10 to 28° C. and even more preferably 15 to 26° C.

The skin cosmetic composition of the present invention preferably has pH 5.5 to 8 at 25° C., more preferably pH 6.0 to 7.8 and even more preferably pH 6.5 to 7.8 in order to form a stable lamellar structure in a cosmetic composition. In the present invention, pH of a sample is directly measured by a pH meter (F-52, manufactured by HORIBA Ltd.) at 25° C.

The skin cosmetic composition of the present invention, can be prepared as, for example, a toning lotion, a milky lotion, a cream, a gel and a beauty essence. The skin cosmetic composition is further preferably used in the form of cream and gel. The skin cosmetic composition can be used as a sheet-form cosmetic in which the skin cosmetic composition is applied on a sheet base such as a woven fabric and a nonwoven fabric or the sheet base is impregnated with the skin cosmetic composition.

The skin cosmetic composition of the present invention can be used by applying it to the skin, preferably the skin except scalp, more specifically a face, a body, arms and legs, and the like.

Furthermore, the skin cosmetic composition of the present invention is used for retaining moisture as well as make the skin glossy by applying it to the skin.

Regarding to the aforementioned embodiment, the present invention will further disclose the following compositions and methods for using them or methods for producing them.

<1> A skin cosmetic composition comprising components (A), (B), (C), (D), (E) and (F):
  (A) from 0.5 to 6% by mass of a linear saturated fatty acid having 12 to 22 carbon atoms,
  (B) from 0.01 to 5% by mass of an organic base,
  (C) from 0.01 to 1% by mass of an inorganic base,
  (D) from 0.5 to 6% by mass of a linear saturated alcohol having 12 to 22 carbon atoms,
  (E) from 0.1 to 20% by mass of an oil agent, and
  (F) water;
and the total amount of components (A) and (D), [(A)+(D)], is from 2.5 to 12% by mass; the mass ratio (A)/[(A)+(D)], which is the mass ratio of component (A) to the total amount of components (A) and (D), [(A)+(D)], is from 0.2 to 0.7; the molar ratio (B)/[(B)+(C)], which is the molar ratio of component (B) to the total amount of components (B) and (C), [(B)+(C)], is from 5 to 60 mol %; and the molar ratio [(B)+(C)]/(A), which is the molar ratio of the total amount of components (B) and (C) to component (A), is from 10 to 80 mol %.

<2> The skin cosmetic composition according to <1>, further comprising (G) a nonionic surfactant in a content of preferably 0.1% by mass or more, more preferably 0.3% by mass or more and even more preferably 0.5% by mass or more, and preferably 2% by mass or less, more preferably 1.5% by mass or less and even more preferably 1.3% by mass or less based on the total composition.

<3> The skin cosmetic composition according to <2>, wherein (G) the nonionic surfactant is preferably at least one compound selected from the group consisting of an ethylene glycol fatty acid ester, a polyethylene glycol fatty acid ester, a polyalkylene glycol alkyl ether, a polyethylene glycol hydrogenated castor oil, a propylene glycol fatty acid ester, a monoglycerin monofatty acid ester, a monoglycerin difatty acid ester, a glycerin alkyl ether, a sorbitan fatty acid ester, a fatty acid alkanolamide and a fatty acid dialkanolamide; more preferably a polyalkylene glycol alkylether; even more preferably a polyalkylene glycol alkyl ether having an alkyl group having 12 to 22 carbon atoms; and further more preferably a polyalkylene glycol alkyl ether having an alkyl group having 12 to 18 carbon atoms.

<4> The skin cosmetic composition according to <2> or <3>, wherein (G) the nonionic surfactant preferably comprises at least two polyalkylene glycol ethers different from each other in the number of carbon atoms by two or more; more preferably comprises at least two compounds selected from the group consisting of a polyethylene glycol ether of lauryl alcohol (laureth-3), a polyethylene glycol ether of cetyl alcohol and a polyethylene glycol ether of stearyl alcohol; even more preferably comprises the above three polyethylene glycol ethers; and further more preferably comprises laureth-3 and ceteareth-20.

<5> The skin cosmetic composition according to <2> or <3>, wherein (G) the nonionic surfactant preferably comprises a mono glycerin mono fatty acid ester such as glycerin monostearate (HLB: 3.4); a glycerin alkyl ether such as glycerin monostearyl ether (HLB: 4.0).

<6> The skin cosmetic composition according to any one of <1> to <5>, wherein component (A) is preferably a linear saturated fatty acid having 14 to 22 carbon atoms; and more preferably a linear saturated fatty acid having 16 to 22 carbon atoms.

<7> The skin cosmetic composition according to any one of <1> to <6>, wherein component (A) is preferably at least one selected from the group consisting of lauric acid, myristic acid, palmitic acid, stearic acid and behenic acid; and more preferably palmitic acid and stearic acid.

<8> The skin cosmetic composition according to any one of <1> to <7>, wherein component (A) comprises two or more linear saturated fatty acids having 12 to 22 carbon atoms different from each other in the number of carbon atoms by two or more.

<9> The skin cosmetic composition according to <8>, wherein the linear saturated fatty acid having 12 to 22 carbon atoms in which the carbon number is larger preferably has 14 to 22 carbon atoms, more preferably 16 to 20 carbon atoms and even more preferably 18 carbon atoms; whereas the linear saturated fatty acid having 12 to 22 carbon atoms in which the carbon number is smaller preferably has 12 to 20 carbon atoms, more preferably 12 to 18 carbon atoms, and even more preferably 12 to 16 carbon atom.

<10> The skin cosmetic composition according to <8> or <9>, wherein the mass ratio of stearic acid contained in component (A) is preferably from 0.2 to 0.8 and more preferably from 0.4 to 0.6.

<11> The skin cosmetic composition according to any one of <1> to <10>, wherein the content of component (A) is preferably 1.5% by mass or more and more preferably 1.8% by mass or more, and preferably 4% by mass or less and more preferably 3.8% by mass or less based on the total composition.

<12> The skin cosmetic composition according to any one of <1> to <11>, wherein component (B) preferably comprises at least one of alkylamine selected from methylamine, ethylamine, propylamine, butylamine, hexylamine, dimethylamine and diethylamine; alkanolamine selected from monoethanolamine, diethanolamine, triethanolamine, N-methyldiethanolamine, N,N-dimethylmonoethanolamine and aminomethyl propanol; and basic amino acid selected from lysine, histidine and arginine.

<13> The skin cosmetic composition according to any one of <1> to <12>, wherein component (B) is preferably an alkanolamine having an alkyl group having 1 to 6 carbon atoms or a basic amino acid having 1 to 6 carbon atoms; more preferably an alkanolamine having an alkyl group having 3 to 6 carbon atoms or a basic amino acid having 3 to 6 carbon atoms; and even more preferably a basic amino acid.

<14> The skin cosmetic composition according to any one of <1> to <13>, wherein component (B) is preferably aminomethyl propanol or arginine, more preferably arginine and even more preferably L-arginine.

<15> The skin cosmetic composition according to any one of <1> to <14>, wherein the content of component (B) is preferably 0.02% by mass or more and more preferably 0.1% by mass or more, and preferably 0.8% by mass or less and more preferably 0.4% by mass or less based on the total composition.

<16> The skin cosmetic composition according to any one of <1> to <15>, wherein component (C) is preferably sodium hydroxide or potassium hydroxide.

<17> The skin cosmetic composition according to any one of <1> to <16>, wherein the content of component (C) is preferably 0.04% by mass or more and more preferably 0.08% by mass or more, and preferably 0.3% by mass or less and more preferably 0.2% by mass or less based on the total composition.

<18> The skin cosmetic composition according to any one of <1> to <17>, wherein component (D) is preferably a linear saturated alcohol having 14 to 22 carbon atoms and more preferably a linear saturated alcohol having 16 to 22 carbon atoms.

<19> The skin cosmetic composition according to any one of <1> to <18>, wherein component (D) is preferably at least one selected from the group consisting of lauryl alcohol, myristyl alcohol, cetyl alcohol, stearyl alcohol and behenyl alcohol, more preferably comprises cetyl alcohol or stearyl alcohol, and even more preferably comprises a mixture of cetyl alcohol and stearyl alcohol.

<20> The skin cosmetic composition according to any one of <1> to <19>, wherein the content of component (D) is preferably 1% by mass or more and more preferably 1.5% by mass or more, and preferably 5.5% by mass or less and more preferably 5.2% by mass or less based on the total composition.

<21> The skin cosmetic composition according to any one of <1> to <20>, wherein component (E) is preferably at least one selected from the group consisting of a hydrocarbon oil, an ether oil, an ester oil, a silicone oil, and a fluorine oil; and more preferably at least one selected from the group consisting of a hydrocarbon oil, an ester oil and a silicone oil; the hydrocarbon oil is preferably at least one selected from the group consisting of liquid paraffin, squalene and vaseline; the ester oil is preferably at least one selected from the group consisting of octyldodecyl myristate, isopropyl palmitate, butyl stearate, di-2-ethylhexyl adipate, neopentyl glycol dicaprate, trioctanoin and alkyl benzoate; and the silicone oil is at least one selected from the group consisting of a dimethylpolysiloxane, a cyclic dimethylpolysiloxane, a methylphenylpolysiloxane, an amino-modified silicone, a carboxy-modified silicone, an alcohol-modified silicone, an alkyl-modified silicone, a polyether-modified silicone and a fluorine-modified silicone.

<22> The skin cosmetic composition according to any one of <1> to <21>, wherein component (E) preferably comprises an oil agent having a refraction index of 1.46 to 1.6, and more preferably comprises an oil agent having a refraction index of 1.48 to 1.58.

<23> The skin cosmetic composition according to <22>, wherein the oil agent having a refraction index of 1.46 to 1.6 is preferably at least one selected from the group consisting of an alkyl benzoate (refraction index: 1.48), a methylphenylpolysiloxane (refraction index: 1.58) and a highly polymerized hydrogenated polyisobutene (number average molecular weight: 1000 to 3000, refraction index: 1.49); more preferably an alkyl benzoate (refraction index: 1.48); even more preferably an alkyl benzoate (refraction index: 1.48) having an alkyl group having 10 to 22 carbon atoms; and further more preferably an alkyl benzoate (refraction index: 1.48) having an alkyl group having 12 to 18 carbon atoms.

<24> The skin cosmetic composition according to any one of <1> to <23>, wherein the content of component (E) is preferably 0.3% by mass or more and more preferably 0.5% by mass or more, and preferably 18% by mass or less and more preferably 16% by mass or less based on the total composition.

<25> The skin cosmetic composition according to any one of <22> to <24>, wherein the content of the oil agent having a refraction index of 1.46 to 1.6 is preferably from 30 to 100% by mass, more preferably from 60 to 100% by mass, even more preferably from 90 to 100% by mass and further more preferably substantially 100% by mass in the component (E).

<26> The skin cosmetic composition according to any one of <1> to <25>, wherein the content of water as component (F) is preferably 50% by mass or more and more preferably 60% by mass or more, and preferably 95% by mass or less and more preferably 90% by mass or less based on the total composition.

<27> The skin cosmetic composition according to any one of <2> to <26>, wherein the mass ratio {[(A)+(D)]/(G)}, which is the mass ratio of the total amount of components (A) and (D), [(A)+(D)], to component (G), is preferably 3 or more, more preferably 4 or more and even more preferably 5 or more, and preferably 30 or less, more preferably 20 or less and even more preferably 10 or less.

<28> The skin cosmetic composition according to any one of <1> to <27>, wherein the total amount of components (A) and (D), [(A)+(D)], is preferably 3% by mass or more and more preferably 4.5% by mass or more, and preferably 9.5% by mass or less and more preferably 8% by mass or less.

<29> The skin cosmetic composition according to any one of <1> to <28>, wherein the mass ratio {(A)/[(A)+(D)]}, which is the mass ratio of component (A) to the total amount of components (A) and (D), [(A)+(D)], is preferably 0.25 or more and more preferably 0.3 or more, and preferably 0.6 or less and more preferably 0.5 or less.

<30> The skin cosmetic composition according to any one of <1> to <29>, wherein the mass ratio {(E)/[(A)+(D)]}, which is the mass ratio of component (E) to the total amount of components (A) and (D), [(A)+(D)], is preferably 0.1 or more, more preferably 0.15 or more and even more preferably 0.2 or more, and preferably 3 or less, more preferably 2 or less and even more preferably 1.5 or less.

<31> The skin cosmetic composition according to any one of <1> to <30>, wherein the molar ratio {(B)/[(B)+(C)]}, which is the molar ratio of component (B) to the total amount of components (B) and (C), [(B)+(C)], is preferably from 8 to 50 mol %, more preferably from 10 to 45 mol % and even more preferably from 15 to 40 mol %.

<32> The skin cosmetic composition according to any one of <1> to <31>, wherein the molar ratio {[(B)+(C)]/(A)}, which is the molar ratio of the total amount of components (B) and (C), [(B)+(C)], to component (A), is preferably from 20 to 70 mol %, more preferably from 25 to 65 mol % and even more preferably from 30 to 60 mol %.

<33> The skin cosmetic composition according to any one of <1> to <32>, wherein pH at 25° C. is preferably from 5.5 to 8, more preferably from 6.0 to 7.8 and even more preferably from 6.5 to 7.8.

<34> The skin cosmetic composition according to any one of <1> to <33>, having a bulk lamellar structure and concentric lamellar structures.

<35> The skin cosmetic composition according to any one of <1> to <34>, wherein the content of the anionic surfactant is preferably 0.01% by mass or more, more preferably 0.1% by mass or more and even more preferably 0.3% by mass or more, and preferably 2% by mass or less, more preferably 1.8% by mass or less and even more preferably 1.5% by mass or less based on the total composition.

<36> The skin cosmetic composition according to any one of <1> to <35>, wherein the content of the solid lipid except components (A) and (D) is preferably 10% by mass or less, more preferably 8% by mass or less, even more preferably 5% by mass or less and further more preferably 3% by mass or less based on the total composition.

<37> A method of using the skin cosmetic composition according to any one of <1> to <36>, comprising applying the skin cosmetic composition to the skin, preferably to skin except scalp and more preferably to any one of a face, a body and arms and legs.

<38> A method of moisturizing the skin, comprising applying the skin cosmetic composition according to any one of <1> to <36> to the skin.

<39> A method of making the skin glossy, comprising applying the skin cosmetic composition according to any one of <1> to <36> to the skin.

<40> A method for producing the skin cosmetic composition according to any one of <1> to <36>, comprising steps 1 to 3:

step 1: mixing components (B), (C) and (F), and then dissolving the mixture at 60 to 100° C. homogeneously to give a water phase, step 2: mixing components (A), (D) and (E), and then dissolving the mixture at 60 to 100° C. homogeneously to give an oil phase, and step 3: mixing the water phase obtained in step 1 and the oil phase obtained in step 2 homogeneously, and then cooling the mixture to preferably 5 to 30° C., more preferably 10 to 28° C. and even more preferably 15 to 26° C.

EXAMPLES

Examples 2 to 27, Comparative Examples 1 to 13

Skin cosmetic compositions were produced in accordance with formulations shown in Table 1 to Table 3, and then whether a lamellar structure was formed in the cosmetic compositions and dry films was observed. Furthermore, the moisture-retaining property (water-holding capacity), crystallization suppression effect, non-slimy feeling and adaptability when the composition was applied, stability, foaming suppression effect when the composition was applied and durability of gloss were evaluated. The results are shown together in Table 1 to Table 3.

(Production Method)

Water-phase components including components (B), (C) and (F) were stirred at 70 to 80° C., and then dissolved to prepare a water phase. Then, oil phase components including components (A), (D) and (E) were stirred at 70 to 80° C., and then dissolved to prepare an oil phase. To the water phase, the oil phase was added while stirring at 70 to 80° C. and thereafter cooled to room temperature (25° C.) while further stirring to produce a skin cosmetic composition (oil-in-water emulsion cosmetic composition).

(Evaluation Method)

(1) Confirmation of Lamellar Structure:

(1-1) Structure Analysis of Cosmetic Composition by Small-Angle X-Ray Diffractometry:

The phase states of cosmetic compositions and dry films were analyzed by small-angle X-ray diffractometry. The dry films were prepared by spreading each of the cosmetic compositions (1 g) by an applicator up to a thickness of 0.1 mm, and then drying it at 20° C. under a 20% RH environment for 24 hours. If repetitive diffraction peaks, which are intrinsic to a lamellar structure, were observed in the obtained X-ray diffraction profile, the sample was indicated by "Y", the sample providing no such peaks was indicated by "N".

(1-2) Confirmation of the Presence of Bulk Lamella and Concentric Lamellas by Polarizing Microscope:

Samples (thickness: 25 mm) was each observed by a polarizing microscope (magnification: 200). If Maltese Cross was observed around oil drops, the sample was indicated by "Y" (concentric lamellas are present); whereas if Maltese Cross was not observed, the sample was indicated by "N". Then, the same samples were observed through a polarizing plate. If a sample wholly looked bright and no crystals were not observed, the sample was indicated by "Y" (bulk lamella is present). If a sample wholly looked bright but crystals were observed, the sample was indicated by "N", and if a sample did not look wholly bright, the sample was indicated by "N".

Figure 2:
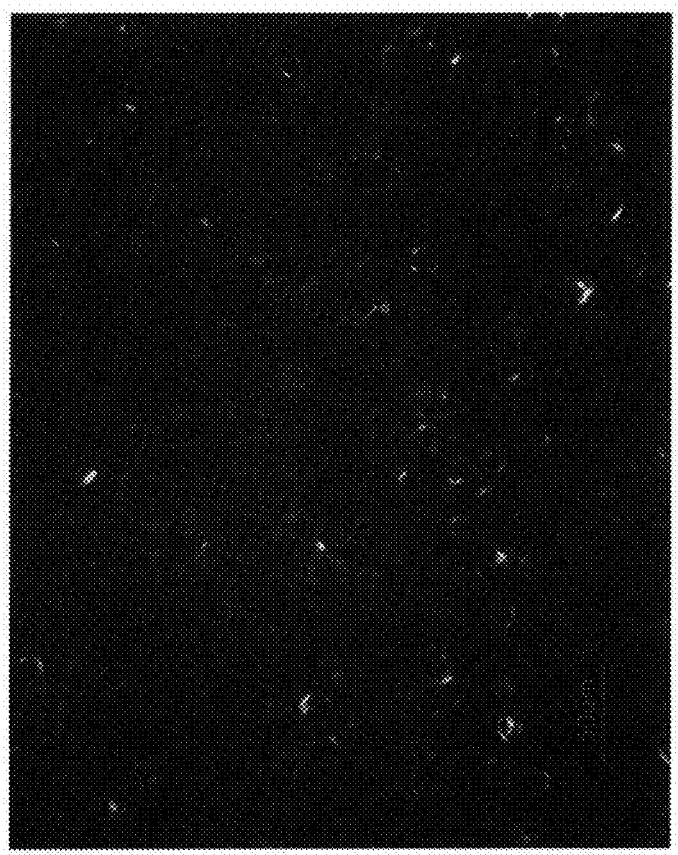
FIG. 2 is a photograph showing a structure of the skin cosmetic composition of Comparative Example 10 observed by a polarizing microscope.
Figure 2:
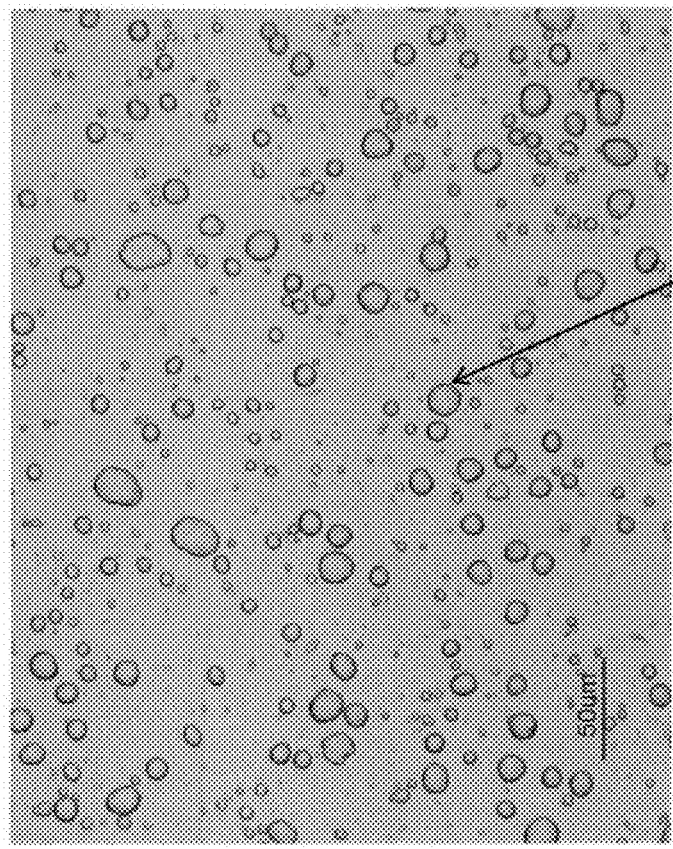

Note that the structures of skin cosmetic compositions according to Example 7 and Comparative Example 10 were observed by a polarizing microscope and photographed. The photographs are shown in FIG. 1 and FIG. 2.

(2) Moisture-Retaining Property (Water-Holding Capacity):

Each cosmetic composition was applied to a 5C quantitative filter (ADVANTEC FILTER PAPER 5C manufactured by Toyo Roshi Kaisha, Ltd.) in a ratio of 0.01 mL/cm$^2$, and then allowed to stand still for 24 hours at 20° C. under a 20% RH environment. The filter was cut and placed on a 40 mL vial bottle (Pierce vial CV-400, manufactured by AS ONE Corporation; the cover has a hole of a diameter of 17.3 mm.), and then the vial was covered. In the vial, a predetermined amount of water was poured. The vial was allowed to stand still under a 20° C. and 20% RH environment for 24 hours. Thereafter, the amount of water loss was measured.

Provided that the mass before storage was represented by (m1) and the mass after 24 hours was represented by (m2), the water evaporation amount from a filter to which a cosmetic composition was not applied was represented by W (g); while the water evaporation amount from a filter to which the cosmetic composition of Example or Comparative Example was applied was represented by S (g), and water evaporation suppression rate (%) was obtained in accordance with the following expression.

Water evaporation amount $W$ (g)=$Wm1$-$Wm2$

Water evaporation amount $S$ (g)=$Sm1$-$Sm2$

Water evaporation suppression rate (%)=($W$ (g)–$S$ (g))/$W$ (g)×100

The higher the numerical value, the better the moisture-retaining property (water-holding capacity).

(3) Crystallization Suppression Effect (Storage Stability):

Skin cosmetic compositions were subjected to a crystal precipitation confirmation test. After preparation, the skin cosmetic compositions were stored at 25° C. under a 40% RH environment for a week. The presence or absence of crystals was checked under polarization light by an optical microscope and evaluated in accordance with the following criteria. In the evaluation, a Mighty vial (No. 7, manufactured by Maruemu Corporation) was used and controlled such that the skin cosmetic composition was kept at a level of 50 mm from the vial bottom.
5: No crystals were observed.
4: Crystals of about less than 1 mm were observed.
3: Crystals of about 1 mm or more and less than 5 mm were observed.
2: Crystals of about 5 mm or more and less than 10 mm were observed.
1: Water separation (level: about 10 mm or less) was observed.

(4) Non-Slimy Feeling and Adaptability when the Skin Cosmetic Composition was Applied:

Each skin cosmetic composition (0.2 mL) was applied to the whole interior side of a front arm of each of 10 special panelists and evaluated for non-slimy feeling and adaptability by them in accordance with the following criteria and evaluation scores were averaged.
5: Skin cosmetic composition is quickly adapted without slimy feeling when applied.
4: Skin cosmetic composition is quickly adapted with slight slimy feeling when applied.
3: Skin cosmetic composition is adapted but slightly slowly with slight slimy feeling when applied.
2: Skin cosmetic composition is adapted but slightly slowly with slimy feeling when applied.
1: Skin cosmetic composition is adapted but slowly with slimy feeling when applied.

(5) Stability of Lamella (Storage Stability):

Skin cosmetic compositions were subjected to a storage stability test. The skin cosmetic compositions were stored at a temperature of 50° C., under a 30% relative-humidity environment for two weeks. Whether water was separated or not was checked under polarization light by an optical microscope, and then evaluated in accordance with the following criteria. In the evaluation, a Mighty vial (No. 7, manufactured by Maruemu Corporation) was used and controlled such that the skin cosmetic composition was kept at a level of 50 mm from the vial bottom.
5: No water separation is observed.
4: Water separation of less than about 1 mm is observed at the bottom.
3: Water separation of about 1 mm or more and less than 5 mm is observed at the bottom.
2: Water separation of about 5 mm or more and less than 10 mm is observed at the bottom.
1: Water separation of about 10 mm or more is observed at the bottom.

(6) Foaming Suppression Effect when the Skin Cosmetic Composition is Applied:

Each skin cosmetic composition (0.2 mL) was applied to the whole interior side of a front arm of each of 10 special panelists and evaluated foaming by them in accordance with the following criteria and evaluation scores were averaged.
5: A cosmetic composition is not foamed when applied; the cosmetic coating film formed after the application is transparent.
4: A cosmetic composition is slightly foamed when applied; however the cosmetic coating film formed after the application is transparent.
3: A cosmetic composition is slightly foamed when applied and the cosmetic coating film formed after the application is slightly whitened.
2: A cosmetic composition is foamed when applied and the cosmetic coating film formed after the application is whitened.
1: A cosmetic composition is foamed when applied and the cosmetic coating film formed after the application is extremely whitened.

(7) Durability of Gloss:

Each skin cosmetic composition (0.05 mL) was applied to the whole back of the hands of 10 special panelists. After they stayed for 8 hours under 10° C. and 50% RH environment, the state of the skin was evaluated in accordance with the following criteria and evaluation scores were averaged.
5: Extremely glossy.
4: Slightly glossy.
3: Substantially not glossy.
2: Substantially not glossy and slightly matte.
1: Not glossy and matte.

TABLE 1

| | Component (% by mass) | Example | | | | | | | | | | | |
|---|---|---|---|---|---|---|---|---|---|---|---|---|---|
| | | 2 | 3 | 4 | 5 | 6 | 7 | 8 | 9 | 10 | 11 | 12 | 13 |
| A | Myristic acid | | | | | | | | | | | | |
| | Stearic acid | 6 | 2 | 3.5 | 3 | 3.5 | 3 | 3.5 | 2.5 | 2.5 | 2.5 | 2.5 | 2.5 |
| | Behenic acid | | | | | | | | | | | | |
| B | L-arginine | 1 | 0.03 | 0.7 | 0.03 | 0.7 | 0.08 | 0.45 | 0.2 | 0.2 | 0.2 | 0.2 | 0.2 |
| | 2-Amino-2-methyl-1-propanol | | | | | | | | | | | | |
| C | Sodium hydroxide | 0.4 | 0.05 | 0.22 | 0.05 | 0.22 | 0.05 | 0.22 | 0.1 | 0.1 | 0.1 | 0.1 | 0.1 |
| D | Myristyl alcohol | | | | | | | | | | | | |
| | Cetostearyl alcohol | 5.2 | 5 | 1.5 | 5 | 4 | 5 | 4 | 4.5 | 4.5 | 4.5 | 4.5 | 4.5 |
| | Behenyl alcohol | | | | | | | | | | | | |
| E | Mineral oil | 18 | 1 | 15 | 1 | 15 | 1 | 15 | 1 | 15 | 5 | | |
| | Isopropyl palmitate | | | | | | | | | | | 5 | |

TABLE 1-continued

| | Component (% by mass) | 2 | 3 | 4 | 5 | 6 | 7 | 8 | 9 | 10 | 11 | 12 | 13 |
|---|---|---|---|---|---|---|---|---|---|---|---|---|---|
| | Dimethicone (10 cs) | | | | | | | | | | | | 5 |
| | Alkyl benzoate (C12-15) (refraction index: 1.48) | | | | | | | | | | | | |
| F | Water | Balance | Balance | Balance | Balance | Balance | Balance | Balance | Balance | Balance | Balance | Balance | Balance |
| G | Laureth-3 | | | | | | | | | | | | |
| | Ceteareth-20 | | | | | | | | | | | | |
| | Diglyceryl laurate | | | | | | | | | | | | |
| | Total | 100 | 100 | 100 | 100 | 100 | 100 | 100 | 100 | 100 | 100 | 100 | 100 |
| | A + D | 11.2 | 7 | 5 | 8 | 7.5 | 8 | 7.5 | 7 | 7 | 7 | 7 | 7 |
| | A/(A + D) mass ratio | 0.54 | 0.29 | 0.70 | 0.38 | 0.47 | 0.38 | 0.47 | 0.36 | 0.36 | 0.36 | 0.36 | 0.36 |
| | B/(B + C) molar ratio | 36.4 | 12.1 | 42.2 | 12.1 | 42.2 | 26.8 | 31.9 | 31.4 | 31.4 | 31.4 | 31.4 | 31.4 |
| | (B + C)/A molar ratio | 74.6 | 20.2 | 77.4 | 13.5 | 77.4 | 16.2 | 65.7 | 41.5 | 41.5 | 41.5 | 41.5 | 41.5 |
| | (A + D)/G mass ratio | — | — | — | — | — | — | — | — | — | — | — | — |
| | E/(A + D) mass ratio | 1.61 | 0.14 | 3.00 | 0.13 | 2.00 | 0.13 | 2.00 | 0.14 | 2.14 | 0.71 | 0.71 | 0.71 |
| | Formation of lamella (preparation): bulk lamella | Y | Y | Y | Y | Y | Y | Y | Y | Y | Y | Y | Y |
| | concentric lamella | Y | Y | Y | Y | Y | Y | Y | Y | Y | Y | Y | Y |
| | Formation of lamella (coating film): bulk lamella | Y | Y | Y | Y | Y | Y | Y | Y | Y | Y | Y | Y |
| | concentric lamella | Y | Y | Y | Y | Y | Y | Y | Y | Y | Y | Y | Y |
| | Moisture-retaining property (water-holding capacity) | 38 | 35 | 36 | 37 | 42 | 38 | 40 | 45 | 42 | 48 | 47 | 47 |
| | Crystallization suppression (storage stability) | 3 | 3 | 3 | 4 | 4 | 4 | 4 | 5 | 5 | 5 | 5 | 5 |
| | Non-slimy feeling and adaptability when applied | 2.3 | 2.5 | 2.3 | 2.7 | 2.2 | 3.1 | 3.4 | 3.3 | 3.4 | 3.7 | 3.6 | 3.7 |
| | Stability of lamella (storage stability) | 3 | 4 | 4 | 4 | 4 | 4 | 4 | 4 | 4 | 4 | 4 | 4 |
| | Whitening resistance when applied (foaming suppression) | 2.3 | 2.7 | 2.7 | 2.6 | 2.6 | 2.9 | 2.8 | 3.3 | 3.4 | 3.4 | 3.7 | 3.8 |
| | Durability of gloss | 2.5 | 2.5 | 2.6 | 2.8 | 2.9 | 2.6 | 2.9 | 2.8 | 2.9 | 3.2 | 3.9 | 3.2 |

TABLE 2

| | Component (% by mass) | 14 | 15 | 16 | 17 | 18 | 19 | 20 | 21 | 22 | 23 | 24 | 25 | 26 | 27 |
|---|---|---|---|---|---|---|---|---|---|---|---|---|---|---|---|
| A | Myristic acid | | | | 2.5 | | | | | | | | | | |
| | Stearic acid | 2.5 | 2.5 | 2.5 | | | 2.5 | 2.5 | 2.5 | 2.5 | 2.5 | 2.5 | 2.5 | 2.5 | 2.5 |
| | Behenic acid | | | | | 2.5 | | | | | | | | | |
| B | L-arginine | 0.2 | 0.2 | 0.2 | 0.2 | 0.2 | | 0.2 | 0.2 | 0.2 | 0.2 | 0.2 | 0.2 | 0.2 | 0.2 |
| | 2-Amino-2-methly-1-propanol | | | | | | 0.2 | | | | | | | | |
| C | Sodium hydroxide | 0.1 | 0.1 | 0.1 | 0.1 | 0.1 | 0.1 | 0.1 | 0.1 | 0.1 | 0.1 | 0.1 | 0.1 | 0.1 | 0.1 |
| D | Myristyl alcohol | | | | 4.5 | | | | | | | | | | |
| | Cetostearyl alcohol | 4.5 | 4.5 | 4.5 | | | | 4.5 | 4.5 | 4.5 | 4.5 | 4.5 | 4.5 | 4.5 | 4.5 |
| | Behenyl alcohol | | | | | 4.5 | | | | | | | | | |
| E | Mineral oil | 5 | 5 | 5 | 5 | 5 | 5 | 5 | 5 | | | | 2.5 | 5 | |
| | Isopropyl palmitate | | | | | | | | | | | | | | |
| | Dimethicone (10 cs) | | | | | | | | | | | | | | |
| | Alkyl benzoate (C12-15) (refraction index: 1.48) | | | | | | | | | 0.5 | 16 | 5 | 2.5 | 5 | 5 |
| F | Water | Balance | Balance | Balance | Balance | Balance | Balance | Balance | Balance | Balance | Balance | Balance | Balance | Balance | Balance |
| G | Laureth-3 | 0.25 | 2 | 1 | 1 | 1 | 1 | | | 1 | 1 | 1 | 1 | 1 | 0.5 |
| | Ceteareth-20 | | | | | | | 1 | | | | | | | 0.5 |
| | Diglyceryl laurate | | | | | | | | 1 | | | | | | |
| | Total | 100 | 100 | 100 | 100 | 100 | 100 | 100 | 100 | 100 | 100 | 100 | 100 | 100 | 100 |
| | A + D | 7 | 7 | 7 | 7 | 7 | 7 | 7 | 7 | 7 | 7 | 7 | 7 | 7 | 7 |
| | A/(A + D) mass ratio | 0.36 | 0.36 | 0.36 | 0.36 | 0.36 | 0.36 | 0.36 | 0.36 | 0.36 | 0.36 | 0.36 | 0.36 | 0.36 | 0.36 |
| | B/(B + C) molar ratio | 31.4 | 31.4 | 31.4 | 31.4 | 31.4 | 47.3 | 31.4 | 31.4 | 31.4 | 31.4 | 31.4 | 31.4 | 31.4 | 31.4 |
| | (B + C)/A molar ratio | 41.5 | 41.5 | 41.5 | 33.3 | 49.7 | 54.0 | 41.5 | 41.5 | 41.5 | 41.5 | 41.5 | 41.5 | 41.5 | 41.5 |

TABLE 2-continued

| Component (% by mass) | Example | | | | | | | | | | | | | |
|---|---|---|---|---|---|---|---|---|---|---|---|---|---|---|
| | 14 | 15 | 16 | 17 | 18 | 19 | 20 | 21 | 22 | 23 | 24 | 25 | 26 | 27 |
| (A + D)/G mass ratio | 28.0 | 3.5 | 7.0 | 7.0 | 7.0 | 7.0 | 7.0 | 7.0 | 7.0 | 7.0 | 7.0 | 7.0 | 7.0 | 7.0 |
| E/(A + D) mass ratio | 0.71 | 0.71 | 0.71 | 0.71 | 0.71 | 0.71 | 0.71 | 0.71 | 0.07 | 2.29 | 0.71 | 0.71 | 1.43 | 0.71 |
| Formation of lamella (preparation): bulk lamella | Y | Y | Y | Y | Y | Y | Y | Y | Y | Y | Y | Y | Y | Y |
| concentric lamella | Y | Y | Y | Y | Y | Y | Y | Y | Y | Y | Y | Y | Y | Y |
| Formation of lamella (coating film): bulk lamella | Y | Y | Y | Y | Y | Y | Y | Y | Y | Y | Y | Y | Y | Y |
| concentric lamella | Y | Y | Y | Y | Y | Y | Y | Y | Y | Y | Y | Y | Y | Y |
| Moisture-retaining property (water-holding capacity) | 50 | 49 | 52 | 45 | 53 | 41 | 50 | 54 | 51 | 52 | 57 | 58 | 63 | 65 |
| Crystallization suppression (storage stability) | 5 | 5 | 5 | 5 | 5 | 4 | 5 | 5 | 5 | 5 | 5 | 5 | 5 | 5 |
| Non-slimy feeling and adaptability when applied | 3.7 | 2.6 | 4.2 | 4.0 | 4.0 | 4.3 | 4.8 | 4.3 | 4.5 | 4.3 | 4.6 | 4.5 | 4.8 | 5.0 |
| Stability of lamella (storage stability) | 4 | 4 | 5 | 4 | 4 | 4 | 5 | 5 | 4 | 3 | 5 | 5 | 5 | 5 |
| Whitening resistance when applied (foaming suppression) | 4.2 | 4.4 | 4.4 | 4.4 | 4.4 | 4.5 | 4.7 | 4.0 | 4.5 | 4.7 | 4.7 | 4.7 | 4.8 | 4.9 |
| Durability of gloss | 4.0 | 3.7 | 4.2 | 4.2 | 4.2 | 4.1 | 4.2 | 4.3 | 3.6 | 4.6 | 4.9 | 4.7 | 4.7 | 5.0 |

TABLE 3

| | Component (% by mass) | Comparative Example | | | | | | | | | | | | |
|---|---|---|---|---|---|---|---|---|---|---|---|---|---|---|
| | | 1 | 2 | 3 | 4 | 5 | 6 | 7 | 8 | 9 | 10 | 11 | 12 | 13 |
| A | Myristic acid | | | | | | | | | | | | | |
| | Stearic acid | | 2.5 | 2.5 | 2 | 0.3 | 0.5 | 7 | 6 | 0.5 | 6 | 0.5 | 6 | 0.5 |
| | Behenic acid | | | | | | | | | | | | | |
| B | L-arginine | 0.2 | 0.2 | | 0.4 | 0.01 | 0.01 | 1 | 1 | 0.005 | 1.5 | 0.01 | 1 | 0.01 |
| | 2-Amino-2-methly-1-propanol | | | | | | | | | | | | | |
| C | Sodium hydroxide | 0.1 | 0.1 | 0.15 | | 0.015 | 0.015 | 0.4 | 0.4 | 0.005 | 1.5 | 0.015 | 0.4 | 0.015 |
| D | Myristyl alcohol | | | | | | | | | | | | | |
| | Cetostearyl alcohol | 4.5 | | 4.5 | 4.5 | 1.4 | 0.3 | 5.2 | 8 | 1.4 | 5.2 | 1.4 | 5.2 | 1.4 |
| | Behenyl alcohol | | | | | | | | | | | | | |
| E | Mineral oil | | | | | 0.3 | 0.3 | 18 | 18 | 0.3 | 18 | | 30 | 0.3 |
| | Isopropyl palmitate | | | | | | | | | | | | | |
| | Dimethicone (10 cs) | | | | | | | | | | | | | |
| | Alkyl benzoate (C12-15) (refraction index: 1.48) | | | | | | | | | | | | | |
| F | Water | Balance | Balance | Balance | Balance | Balance | Balance | Balance | Balance | Balance | Balance | Balance | Balance | Balance |
| G | Laureth-3 | | | | | | | | | | | | | |
| | Ceteareth-20 | | | | | | | | | | | | | |
| | Diglyceryl laurate | | | | | | | | | | | | | |
| | Total | 100 | 100 | 100 | 100 | 100 | 100 | 100 | 100 | 100 | 100 | 100 | 100 | 100 |
| | A + D | 4.5 | 2.5 | 7 | 6.5 | 1.7 | 0.8 | 12.2 | 14 | 1.9 | 11.2 | 1.9 | 11.2 | 1.9 |
| | A/(A + D) mass ratio | 0.00 | 1.0 | 0.36 | 0.31 | 0.18 | 0.63 | 0.57 | 0.43 | 0.26 | 0.54 | 0.26 | 0.54 | 0.26 |
| | B/(B + C) molar ratio | 31.4 | 31.4 | 0.0 | 100.0 | 13.3 | 13.3 | 36.4 | 36.4 | 18.6 | 18.6 | 13.3 | 36.4 | 13.3 |
| | (B + C)/A molar ratio | — | 41.5 | 42.7 | 32.7 | 41.0 | 24.6 | 64.0 | 74.6 | 8.7 | 218.6 | 24.6 | 74.6 | 24.6 |
| | (A + D)/G mass ratio | — | — | — | — | — | — | — | — | — | — | — | — | — |
| | E/(A + D) mass ratio | 0.0 | 0.0 | 0.0 | 0.0 | 0.18 | 0.38 | 1.48 | 1.29 | 0.16 | 1.61 | 0.00 | 2.68 | 0.16 |
| | Formation of lamella (preparation): bulk lamella | N | N | N | Y | N | N | Y | Y | N | N | N | N | Y |
| | concentric lamella | N | Y | Y | N | N | N | Y | Y | N | Y | N | Y | Y |
| | Formation of lamella (coating film): bulk lamella | N | N | N | Y | N | N | Y | Y | N | N | N | N | Y |
| | concentric lamella | N | Y | Y | N | N | N | Y | Y | N | Y | N | Y | Y |
| | Moisture-retaining property (water-holding capacity) | 5 | 12 | 25 | 32 | 10 | 12 | 30 | 35 | 8 | 25 | 15 | 20 | 35 |
| | Crystallization suppression (storage stability) | 1 | 1 | 1 | 2 | 2 | 2 | 2 | 1 | 2 | 2 | 2 | 1 | 3 |

TABLE 3-continued

| Component (% by mass) | Comparative Example | | | | | | | | | | | | |
|---|---|---|---|---|---|---|---|---|---|---|---|---|---|
| | 1 | 2 | 3 | 4 | 5 | 6 | 7 | 8 | 9 | 10 | 11 | 12 | 13 |
| Non-slimy feeling and adaptability when applied | 1.3 | 1.5 | 2.1 | 1.4 | 2.1 | 2.0 | 1.3 | 1.2 | 2.1 | 1.3 | 2.1 | 1.7 | 2.6 |
| Stability of lamella (storage stability) | 1 | 2 | 2 | 2 | 1 | 1 | 1 | 1 | 1 | 1 | 2 | 1 | 3 |
| Whitening resistance when applied (foaming suppression) | 1.4 | 1.4 | 1.3 | 1.3 | 1.2 | 1.6 | 1.4 | 1.4 | 1.2 | 1.1 | 1.4 | 1.6 | 2.4 |
| Durability of gloss | 1.7 | 1.7 | 1.6 | 1.8 | 1.6 | 1.7 | 1.7 | 1.5 | 1.4 | 1.5 | 1.8 | 1.5 | 2.3 |

Examples 28 to 37

In the same manner as in Examples 1 to 27, oil-in-water emulsion compositions (milky lotion) were produced in accordance with the formulations shown in Table 4 and whether a lamellar structure was formed in the cosmetic compositions and dry films was observed. Furthermore, the moisture-retaining property (water-holding capacity), crystallization suppression effect, non-slimy feeling and adaptability when the composition was applied, storage stability, foaming suppression effect when the composition was applied and durability of gloss were evaluated. The results are shown together in Table 4.

TABLE 4

| | Component (% by mass) | Example | | | | | | | | | |
|---|---|---|---|---|---|---|---|---|---|---|---|
| | | 28 | 29 | 30 | 31 | 32 | 33 | 34 | 35 | 36 | 37 |
| A | Myristic acid | 1.25 | | | | | | | | | |
| | Palmitic acid | | 2 | 1.25 | 0.5 | | | | | | |
| | Stearic acid | 1.25 | 0.5 | 1.25 | 2 | 1.25 | 2.5 | 2.5 | 2.5 | 2.5 | 0.6 |
| | Behenic acid | | | | | 1.25 | | | | | |
| B | L-arginine | 0.2 | 0.2 | 0.2 | 0.2 | 0.2 | 0.2 | 0.2 | 0.2 | 0.2 | 0.015 |
| C | Sodium hydroxide | 0.1 | 0.1 | 0.1 | 0.1 | 0.1 | 0.1 | 0.1 | 0.1 | 0.1 | 0.02 |
| D | Cetostearyl alcohol | 4.5 | 4.5 | 4.5 | 4.5 | 4.5 | 4.5 | 4.5 | 4.5 | 4.5 | 1.9 |
| E | Mineral oil | 5 | 5 | 5 | 5 | 5 | 5 | 5 | 5 | 5 | 0.3 |
| F | Water | Balance | Balance | Balance | Balance | Balance | Balance | Balance | Balance | Balance | Balance |
| G | Laureth-3 | 1 | 1 | 1 | 1 | 1 | | | 0.5 | | |
| | Cetareth-20 | | | | | | | | | 0.5 | |
| | Glyceryl stearate | | | | | | 1 | | 0.5 | 0.5 | |
| | Stearyl glyceryl ether | | | | | | | 1 | | | |
| | Total | 100 | 100 | 100 | 100 | 100 | 100 | 100 | 100 | 100 | 100 |
| | A + D | 7 | 7 | 7 | 7 | 7 | 7 | 7 | 7 | 7 | 2.5 |
| | A/(A + D) mass ratio | 0.36 | 0.36 | 0.36 | 0.36 | 0.36 | 0.36 | 0.36 | 0.36 | 0.36 | 0.24 |
| | B/(B + C) molar ratio | 37.3 | 37.3 | 37.3 | 37.3 | 37.3 | 37.3 | 37.3 | 37.3 | 37.3 | 14.0 |
| | (B + C)/A molar ratio | 37.0 | 38.2 | 39.4 | 40.6 | 45.2 | 41.5 | 41.5 | 41.5 | 41.5 | 27.8 |
| | (A + D)/G mass ratio | 7.0 | 7.0 | 7.0 | 7.0 | 7.0 | 7.0 | 7.0 | 7.0 | 7.0 | — |
| | E/(A + D) mass ratio | 0.71 | 0.71 | 0.71 | 0.71 | 0.71 | 0.71 | 0.71 | 0.71 | 0.71 | 0.12 |
| | Formation of lamella (preparation): bulk lamella | Y | Y | Y | Y | Y | Y | Y | Y | Y | Y |
| | concentric lamella | Y | Y | Y | Y | Y | Y | Y | Y | Y | Y |
| | Formation of lamella (coating film): bulk lamella | Y | Y | Y | Y | Y | Y | Y | Y | Y | Y |
| | concentric lamella | Y | Y | Y | Y | Y | Y | Y | Y | Y | Y |
| | Moisture-retaining property (water-holding capacity) | 50 | 54 | 60 | 56 | 58 | 56 | 52 | 58 | 57 | 36 |
| | Crystallization suppression (storage stability) | 5 | 5 | 5 | 5 | 5 | 5 | 5 | 5 | 5 | 3 |
| | Non-slimy feeling and adaptability when applied | 4.2 | 4.3 | 4.4 | 4.3 | 4.5 | 4.5 | 4.4 | 4.6 | 4.7 | 2.6 |
| | Stability of lamella (storage stability) | 5 | 5 | 5 | 5 | 5 | 5 | 5 | 5 | 5 | 3 |
| | Whitening resistance when applied (foaming suppression) | 4.4 | 4.4 | 4.5 | 4.5 | 4.4 | 4.3 | 4.2 | 4.6 | 4.5 | 2.5 |
| | Durability of gloss | 4.3 | 4.2 | 4.4 | 4.2 | 4.2 | 4.4 | 4.2 | 4.5 | 4.4 | 2.4 |

Examples 38 and 39

In the same manner as in Examples 1 to 27, oil-in-water emulsion compositions (milky lotion) were produced in accordance with the formulations shown in Tables 5 and 6, and then whether a lamellar structure was formed in the cosmetic compositions and dry films was observed. Furthermore, the moisture-retaining property (water-holding capacity), crystallization suppression effect, non-slimy feeling and adaptability when the composition was applied, storage stability, foaming suppression effect when the composition was applied and durability of gloss were evaluated. The results are shown together in Tables 5 and 6.

TABLE 5

| | (Component) | (% by mass) |
|---|---|---|
| A | Stearic acid | 2.5 |
| B | L-arginine | 0.2 |
| C | Sodium hydroxide | 0.1 |
| D | Cetostearyl alcohol | 4.5 |
| | Glycerin | 5 |
| E | Alkyl benzoate (C12-15) (refraction index: 1.48) | 5 |
| | Vaseline | 2 |
| | Mineral oil | 2 |
| | Dimethicone (10 Cst) | 2 |
| G | Ceteareth-20 | 0.5 |
| | Laureth-3 | 0.5 |
| | Aluminum starch/octenyl succinate | 1 |
| | Carbomer 981 * | 0.1 |
| | Methyl paraben | 0.2 |
| | Fragrance | 0.07 |
| F | Water | Balance |
| | Total | 100 |
| | A + D | 7 |
| | A/(A + D) mass ratio | 0.36 |
| | B/(B + C) molar ratio | 31.43 |
| | (B + C)/A molar ratio | 41.52 |
| | (A + D)/G mass ratio | 7 |
| | E/(A + D) mass ratio | 1.57 |
| | Formation of lamella (preparation): bulk lamella | Y |
| | concentric lamella | Y |
| | Formation of lamella (coating film): bulk lamella | Y |
| | concentric lamella | Y |
| | Moisture-retaining property (water-holding capacity) | 67 |
| | Crystallization suppression (storage stability) | 5 |
| | Non-slimy feeling and adaptability when applied | 5 |
| | Stability of lamella (storage stability) | 5 |
| | Whitening resistance when applied (foaming suppression) | 4.8 |
| | Durability of gloss | 5 |

* Acrylic acid homopolymer (manufactured by Lubrizol Advanced Materials, Inc.)

TABLE 6

| | (Component) | (% by mass) |
|---|---|---|
| A | Stearic acid | 3 |
| B | L-arginine | 0.2 |
| C | Sodium hydroxide | 0.3 |
| D | Cetostearyl alcohol | 4 |
| | Glycerin | 4 |
| E | Alkyl benzoate (C12-15) (refraction index: 1.48) | 5 |
| | Vaseline | 3 |
| | Mineral oil | 0.5 |
| | Hydrogenated polydecene | 0.5 |
| | Ethylhexyl isononate | 0.5 |
| | Octyldodecyl myristate | 1.5 |
| | Shea butter | 2 |
| | Dimethicone (10 Cst) | 1.7 |
| | Cetyl ester wax | 0.5 |
| G | Ceteareth-20 | 0.5 |
| | Carbomer 981 * | 0.1 |
| | Methyl paraben | 0.4 |
| | Fragrance | 0.15 |
| F | Water | Balance |
| | Total | 100 |
| | A + D | 7 |
| | A/(A + D) mass ratio | 0.43 |
| | B/(B + C) molar ratio | 13.26 |
| | (B + C)/A molar ratio | 82.01 |
| | (A + D)/G mass ratio | 14 |
| | E/(A + D) mass ratio | 2.1 |
| | Formation of lamella (preparation): bulk lamella | Y |
| | concentric lamella | Y |
| | Formation of lamella (coating film): bulk lamella | Y |
| | concentric lamella | Y |
| | Moisture-retaining property (water-holding capacity) | 58 |
| | Crystallization suppression (storage stability) | 5 |
| | Non-slimy feeling and adaptability when applied | 4.6 |
| | Stability of lamella (storage stability) | 4 |
| | Whitening resistance when applied (foaming suppression) | 4.8 |
| | Durability of gloss | 5 |

* Acrylic acid homopolymer (manufactured by Lubrizol Advanced Materials, Inc.)

What is claimed is:

1. A skin cosmetic composition comprising the following components (A), (B), (C), (D), (E) and (F):
    (A) from 0.5 to 6% by mass of a linear saturated fatty acid having 12 to 22 carbon atoms,
    (B) from 0.01 to 5% by mass of an organic base,
    (C) from 0.01 to 1% by mass of an inorganic base,
    (D) from 0.5 to 6% by mass of a linear saturated alcohol having 12 to 22 carbon atoms,
    (E) from 0.1 to 20% by mass of an oil agent, and
    (F) water,
wherein a total amount of components (A) and (D), [(A)+(D)], is from 2.5 to 12% by mass; a mass ratio (A)/[(A)+(D)], which is a mass ratio of component (A) to the total amount of components (A) and (D), [(A)+(D)], is from 0.2 to 0.7; a molar ratio (B)/[(B)+(C)], which is a molar ratio of component (B) to a total amount of components (B) and (C), [(B)+(C)], is from 5 to 60 mol %; and a molar ratio [(B)+(C)]/(A), which is a molar ratio of the total amount of components (B) and (C), [(B)+(C)], to component (A), is from 10 to 80 mol %.

2. The skin cosmetic composition according to claim 1, further comprising (G) a nonionic surfactant (G) in a content of 0.1 to 2% by mass.

3. The skin cosmetic composition according to claim 1, wherein component (A) is a linear saturated fatty acid having 14 to 22 carbon atoms.

4. The skin cosmetic composition according to claim 1, wherein component (A) comprises two or more linear saturated fatty acids having 12 to 22 carbon atoms different from each other in the number of carbon atoms by two or more.

5. The skin cosmetic composition according to claim 1, wherein component (B) is an aminomethyl propanol or a basic amino acid.

6. The skin cosmetic composition according to claim 1, wherein component (B) is L-arginine.

7. The skin cosmetic composition according to claim 1, wherein component (C) is sodium hydroxide or potassium hydroxide.

8. The skin cosmetic composition according to claim 1, wherein component (D) is a linear saturated alcohol having 14 to 22 carbon atoms.

9. The skin cosmetic composition according to claim 1, wherein component (E) comprises at least one selected from the group consisting of a hydrocarbon oil, an ester oil and a silicone oil.

10. The skin cosmetic composition according to claim 1, wherein component (E) comprises an oil agent having a refraction index of 1.46 to 1.6.

11. The skin cosmetic composition according to claim 2, wherein a mass ratio $\{[(A)+(D)]/(G)\}$, which is a mass ratio of the total amount of components (A) and (D), [(A)+(D)], to component (G), is from 3 to 30.

12. The skin cosmetic composition according to claim 1, wherein a mass ratio $\{(E)/[(A)+(D)]\}$, which is a mass ratio of component (E) to the total amount of components (A) and (D), [(A)+(D)], is from 0.1 to 3.

13. The skin cosmetic composition according to claim 1, having a bulk lamellar structure and a concentric lamella structure.

14. A method of using the skin cosmetic composition according to claim 1, comprising applying the skin cosmetic composition to skin.

15. A method for producing the skin cosmetic composition according to claim 1, comprising steps 1 to 3:
- step 1: mixing components (B), (C) and (F), and then dissolving the mixture at 60 to 100° C. homogeneously to give a water phase,
- step 2: mixing components (A), (D) and (E), and then dissolving the mixture at 60 to 100° C. homogeneously to give an oil phase, and
- step 3: mixing the water phase obtained in step 1 and the oil phase obtained in step 2 homogeneously, and then cooling the mixture to 5 to 30° C.

* * * * *